(12) United States Patent
Olbert et al.

(10) Patent No.: US 6,747,162 B2
(45) Date of Patent: Jun. 8, 2004

(54) COUNTERFLOW REACTOR WITH A BUNDLE OF CONTACT TUBES

(75) Inventors: Gerhard Olbert, Dossenheim (DE); Franz Corr, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/276,223

(22) PCT Filed: May 3, 2001

(86) PCT No.: PCT/EP01/04975

§ 371 (c)(1),
(2), (4) Date: Nov. 14, 2002

(87) PCT Pub. No.: WO01/87476

PCT Pub. Date: Nov. 22, 2001

(65) Prior Publication Data

US 2003/0147788 A1 Aug. 7, 2003

(30) Foreign Application Priority Data

May 17, 2000 (DE) .......................................... 100 24 342

(51) Int. Cl.⁷ ....................... F28D 15/00; C07D 307/89; C07C 51/25
(52) U.S. Cl. ....................... 549/248; 549/256; 562/545; 568/475; 568/476; 422/201
(58) Field of Search .......................... 422/201; 549/248, 549/256; 562/545; 568/475, 476

(56) References Cited

U.S. PATENT DOCUMENTS

| 2,345,423 | A | 3/1944 | Pfannmueller |
| 3,566,961 | A | 3/1971 | Lorenz et al. |
| 3,760,870 | A | 9/1973 | Guetlhuber |
| 3,871,445 | A | 3/1975 | Wanka et al. |
| 4,657,741 | A | 4/1987 | Vogl |

FOREIGN PATENT DOCUMENTS

| DE | 402 529 | 10/1923 |
| DE | 16 01 162 | 10/1970 |
| DE | 34 09 159 | 9/1985 |
| DE | 198 36792 | 2/2000 |
| GB | 310 157 | 4/1929 |
| GB | 310 175 | 4/1929 |
| GB | 667167 | 2/1952 |

OTHER PUBLICATIONS

Derwent Abst. 90273Y/51.
Abst. 3409–159.

*Primary Examiner*—Bernard Dentz
(74) *Attorney, Agent, or Firm*—Keil & Weinkauf

(57) ABSTRACT

In a reactor (1) which has a bundle of catalyst tubes (2) and in which a heat transfer medium is circulated through the space surrounding the catalyst tubes, with the ring lines (3, 4) at both ends of the reactor with openings (5, 6) through the wall for introduction or removal of a heat transfer medium by means of one or more pumps, where the heat transfer medium is introduced into the lower ring line (4) and is returned via the upper ring line (3) to the pump(s) and the heat transfer medium or a substream of the heat transfer medium may, if desired, be passed over one or more external heat exchangers, and with deflecting plates (7) which alternately leave free an open cross section in the middle of the reactor and at the edge of the reactor, the lower ring line (4) is divided by means of a horizontal dividing wall (8) into two regions between which material can pass via preferably uniformly distributed openings (9) having a regulatable open cross section.

13 Claims, 6 Drawing Sheets

FIG.4 C-C

COUNTERFLOW REACTOR WITH A BUNDLE OF CONTACT TUBES

Figure 1:
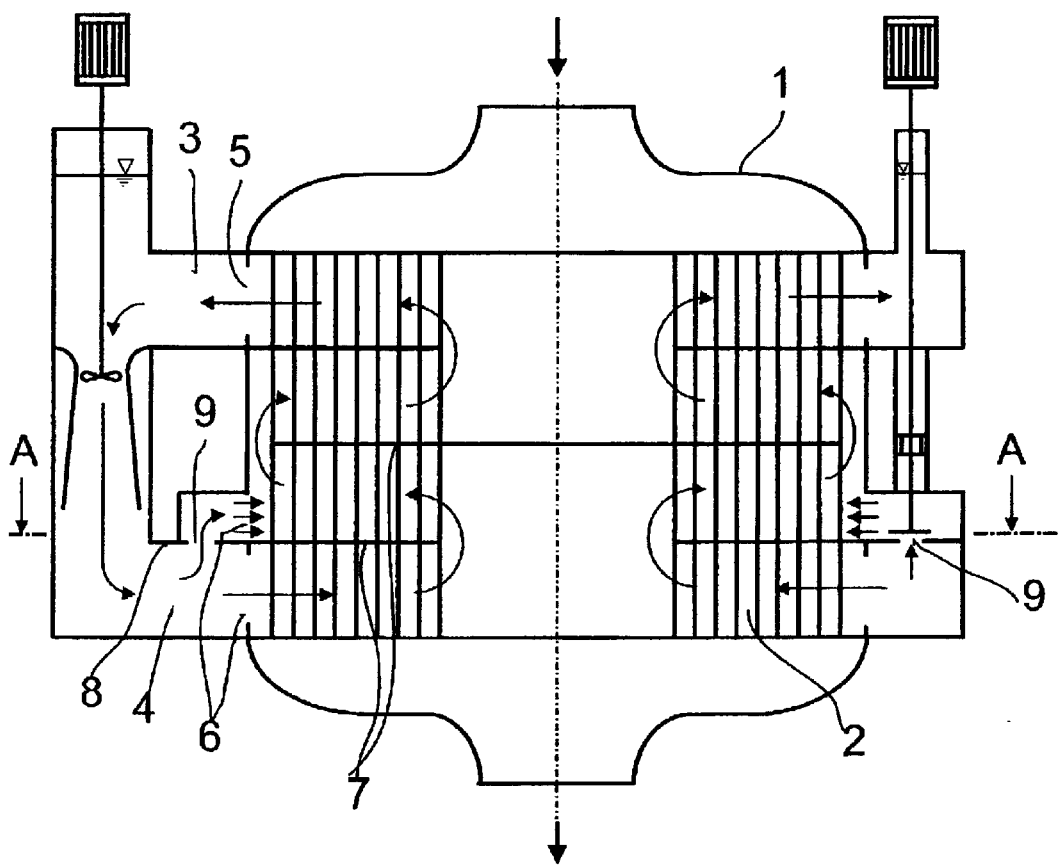

This application is a 371 of PCT/EP01/04975 filed May 3, 2001.

The present invention relates to a reactor which has a bundle of catalyst tubes and in which a heat transfer medium is circulated through the space surrounding the catalyst tubes, and to the use of the reactor for carrying out oxidation reactions.

The customary construction of such reactors comprises a generally cylindrical vessel in which a bundle, i.e. a multiplicity, of catalyst tubes is accommodated, usually in a vertical arrangement. These catalyst tubes which may contain supported catalysts are, at their ends, fixed to and sealed into tube plates and each open into a cap joined to the vessel at its upper or lower end. The reaction mixture flowing through the catalyst tubes is introduced and removed via these caps. A heat transfer medium is circulated through the space surrounding the catalyst tubes in order to level out the heat balance, particularly in the case of strongly exothermic reactions.

For economic reasons, reactors having a very large number of catalyst tubes are used, with the number of catalyst tubes accommodated in the reactor frequently being in the range from 10,000 to 50,000.

As regards the heat transfer medium circuit, it is known that a largely homogeneous temperature distribution in the heat transfer medium across each horizontal section through the reactor should be achieved so that virtually all catalyst tubes participate uniformly in the reaction (e.g. DE-C 16 01 162). The smoothing of the temperature distribution is achieved by introduction of heat or removal of heat via external ring lines which are installed at each of the ends of the reactor and have a multiplicity of openings through the wall, as described, for example, in DE-C 34 09 159.

A further improvement in heat transfer is achieved by installation of deflecting plates which alternately leave free an open cross section in the middle of the reactor and at the edge of the reactor. Such an arrangement is suitable, in particular, for annular tube bundles having a free central space and is known, for example, from GB-B 31 01 57.

In large reactors which have a number of catalyst tubes in the above mentioned range from about 10,000 to 50,000 and are additionally fitted with deflecting plates, the pressure drop of the heat transfer medium is comparatively very large. Thus, the eutectic salt melt of potassium nitrate and sodium nitrite frequently used for removal of the heat liberated in oxidation reactions, which has a water-like viscosity at a use temperature of preferably from about 250° C. To 400° C., has to be pumped with a head of from about 4 to 5 m into a reactor of the above mentioned size in order to overcome the pressure drop.

In such large reactors, the pump system is advantageously located between the upper ring line and the lower ring line, with the heat transfer medium being fed into the lower region of the reactor, for example, via a ring line.

The reaction mixture is customarily passed through the catalyst-filled catalyst tubes from the top downward. As the reaction progress in the catalyst tubes, a temperature profile with a temperature maximum (hot spot) in the initial region of the tubes through which the reaction mixture flows is established. A particular problem here is that the activity of the catalyst drops with increasing operating time and as a consequence the hot spot region migrates from the top downward through the reaction tubes.

It is an object of the present invention, starting from a single external heat transfer medium circuit, to achieve a heat transfer medium flow which can be regulated over the height of the reactor and as the reaction progresses.

The achievement of this object starts out from a reactor which has a bundle of catalyst tubes and in which a heat transfer medium is circulated through the space surrounding the catalyst tubes, with ring lines at both ends of the reactor with openings through the wall for introduction or removal of a heat transfer medium by means of one or more pumps, where the heat transfer medium is introduced into the lower ring line and is returned via the upper ring line to the pump(s) and the heat transfer medium or a substream of the heat transfer medium may, if desired, be passed over one or more external heat exchangers, and with deflecting plates which alternately leave free an open cross section in the middle of the reactor and at the edge of the reactor.

In the reactor of the present invention, the lower ring line is divided by means of a horizontal dividing wall into two regions between which material can pass via preferably uniformly distributed openings.

In a further variant of the reactor of the present invention, at least one radial chamber which extends over the entire height of the reactor and has a regulatable feed opening for the heat transfer medium from the lower ring line and a central outlet for the heat transfer medium at a set table height in the middle of the reactor is provided.

The reactors of the present invention ensure, by means of simple constructional measures, an increased degree of operational safety combined with an extension of the catalyst life and an increase in capacity and selectivity.

This is achieved according to the present invention by the lower ring line via which the heat transfer medium is introduced into the reactor being divided by means of a horizontal dividing wall into two regions which are connected to one another via openings. The horizontal dividing wall can in principle be located at any height in the lower ring line, but preference is given to a symmetrical division into two equal regions. Likewise the openings to be provided in the horizontal dividing wall can in principle be of any number and size, but they are preferably distributed uniformly. The geometry of the openings is preferably circular, with the openings particularly preferably widening conically toward the top. The openings have preferably a regulatable open cross section, with slide gates or valves which are controllable via a regulating drive being used in a known manner for regulation. The openings can also have fixed open cross sections. The number and size of the openings is preferably such that a proportion of from 0 to 70%, preferably from 20 to 50%, of the heat transfer medium flow enters the upper region of the lower ring line directly.

In a preferred embodiment, one or more further ring lines for the introduction in each case of regulatable substreams of the heat transfer medium stream from the lower ring line via regulatable openings in the horizontal dividing wall of the lower ring line and also suitable feed lines to the further ring lines are provided, distributed over the height of the reactor, in the region between the lower ring line and the upper ring line. The further ring lines are particularly preferably distributed symmetrically over the height of the reactor. More preferably, two or three further ring lines are used. The substreams to be separated off can in principle each represent any proportion of the heat transfer medium stream introduced into the lower ring line. Particular preference is given to in each case separating off a proportion of from 0 to 70%, preferably from 20 to 30%, of the heat transfer medium stream introduced.

In a further embodiment, a radial chamber which extends over the entire height of the reactor and has a regulatable feed opening for the heat transfer medium from the lower ring line and a central outlet for the heat transfer medium at a set table height in the middle of the reactor is provided. Industrial implementation of this embodiment is carried out particularly simply by providing a tube-free space of essentially any width, preferably a width in the range from 100 mm to 500 mm, in particular 100 mm over the entire height of the reactor along a reactor diameter. The heat transfer medium is introduced into this tube-free space at the circumference of the reactor, from the lower ring channel via openings having a regulatable open cross section. The inflow of heat transfer medium is preferably regulated by means of an actuating drive which has a shut-off device, in particular a slide gate or a valve.

Complete separation of the heat transfer medium in the region between the reaction tubes is not necessary. Even the catalyst tubes themselves, which are generally installed at the highest possible density for cost reasons, generally at a ratio of spacing, i.e. a distance between two nearest-neighbor tubes, to external tube diameter in the range from 1.26 to about 1.6, substantially deflect the major part of the heat transfer medium stream into the tube-free middle of the reactor for hydrodynamic reasons. In addition, it is possible to provide parallel side walls for separating the chamber from the reactor space fitted with catalyst tubes, but it is not necessary for these side walls to be liquid-tight.

The central outlet for the heat transfer medium in the middle of the reactor can in principle be located at any desired height; matching the temperature profile to the reaction to be carried out is, in particular, a decisive factor in this choice.

The regulation of the heat transfer medium flow via the lower ring channel by means of a horizontal dividing wall or via additional ring channels distributed over the height of the reactor is particularly preferably combined with the regulation of the heat transfer medium flow via the middle of the reactor by means of a radial chamber.

It is also possible to provide a further radial chamber which is arranged at an angle of 90° to the first radial chamber, thus forming a cross arrangement.

It can be advantageous to install static mixers in one or all regions in the middle of the reactor where the deflecting plates leave free an open cross section. In this way, an increased temperature across the reactor cross section is achieved; in particular, inequalities in the temperature distribution over the two halves of the reactor are levelled out. There are in principle no restrictions in respect of the static mixers which can be used; particular preference is given to static mixers having ring- or plate-shaped internals which may, in particular, be perforated or corrugated.

The reactor is not limited in terms of the type of heat transfer medium, which can be used either for the removal of heat, i.e. for carrying out exothermic reactions, and also for the supply of heat to the reaction mixture flowing through the catalyst tubes, i.e. for carrying out endothermic reactions.

The reactor is particularly suitable for carrying out oxidation reactions, in particular for preparing phthalic anhydride, maleic anhydride, glyoxal, (meth)acrolein and (meth)acrylic acid.

Figure 1A:
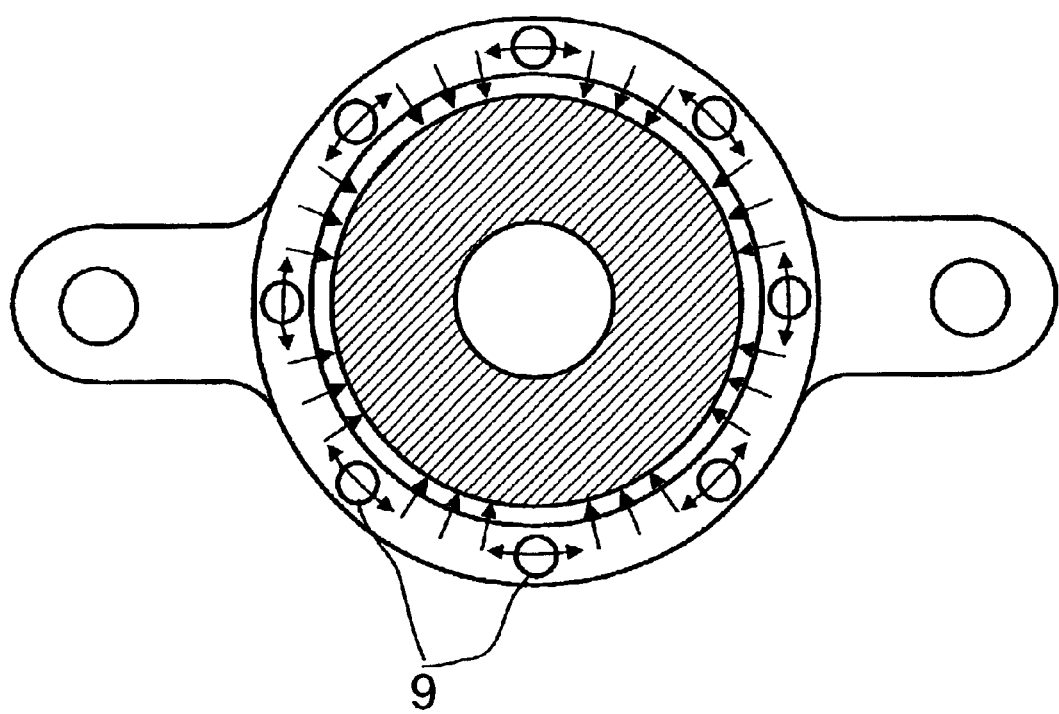
Figure 2:
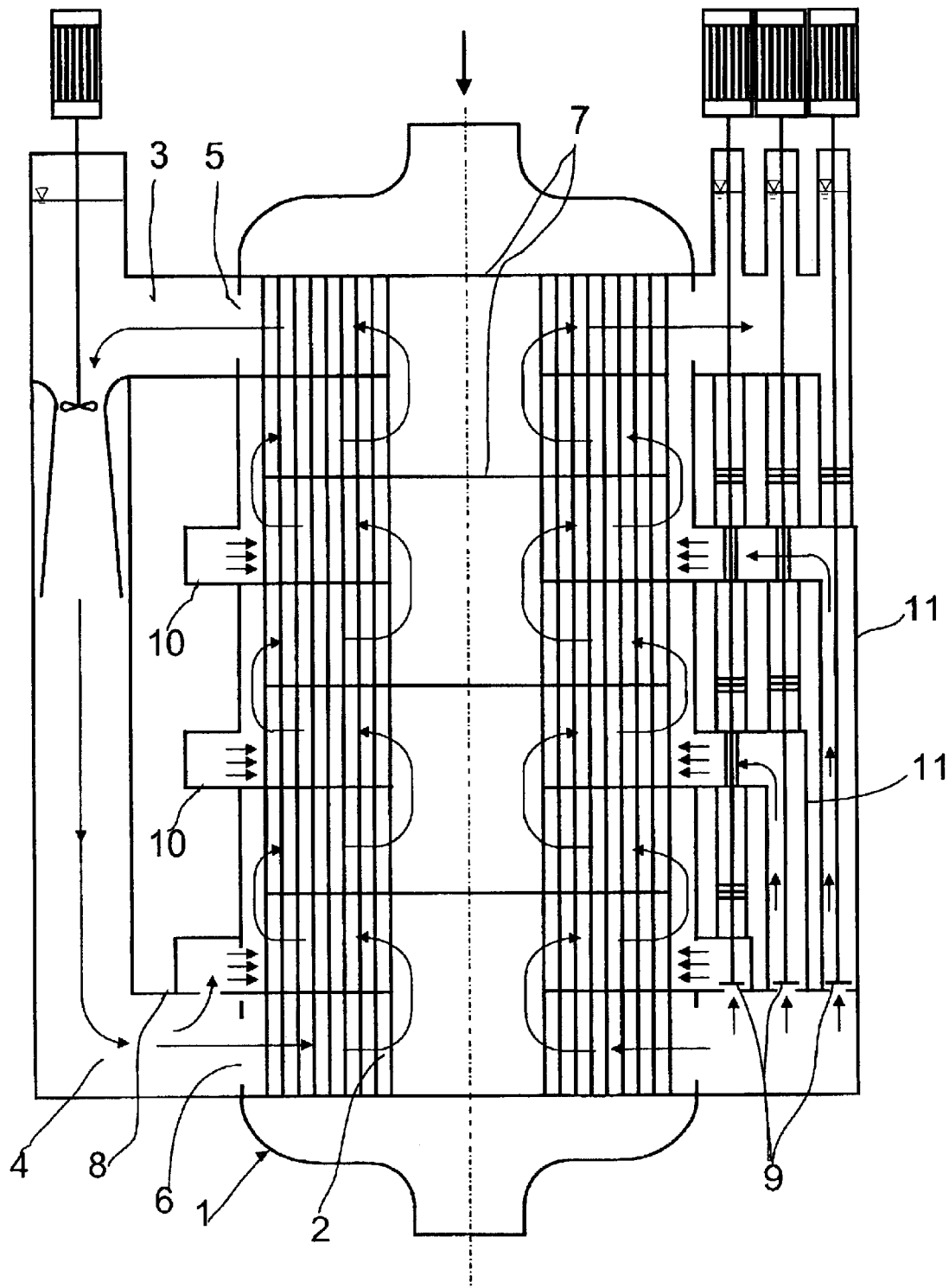
Figure 3:
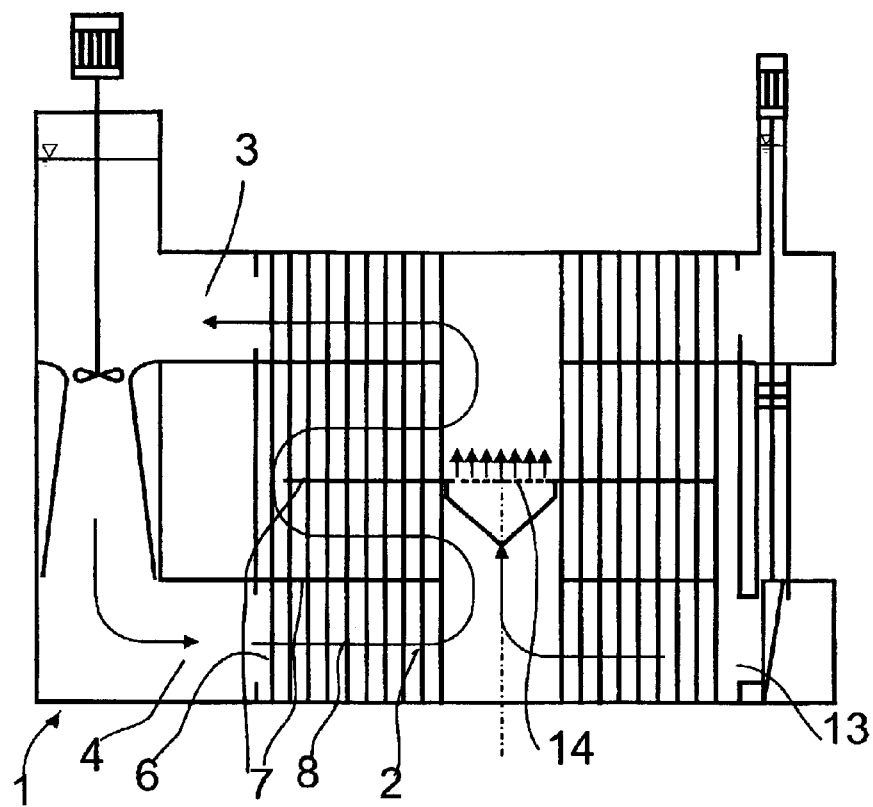
Figure 3A:
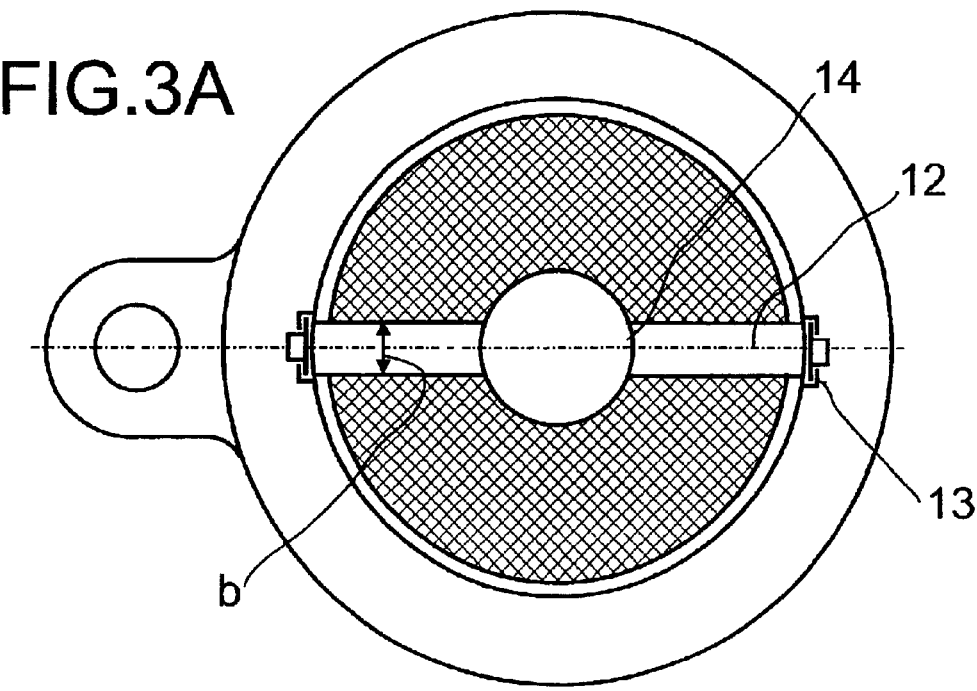
Figure 4A:
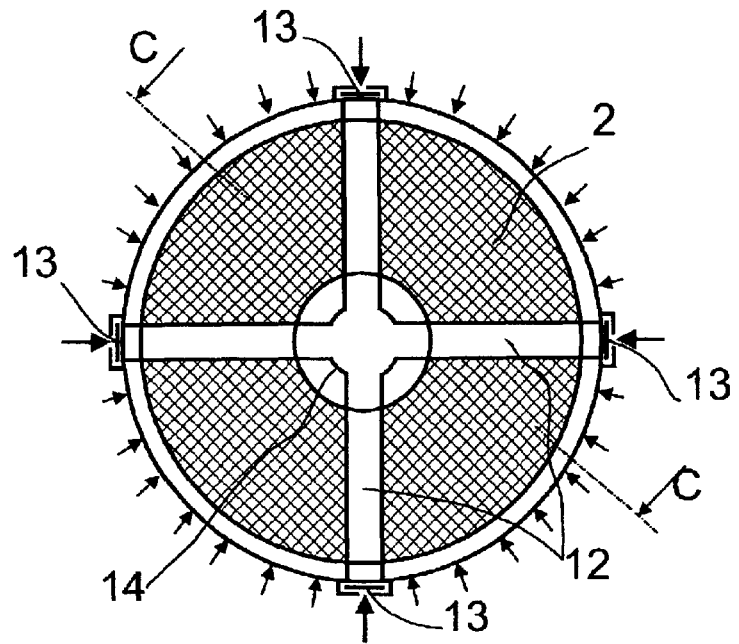
Figure 4A:
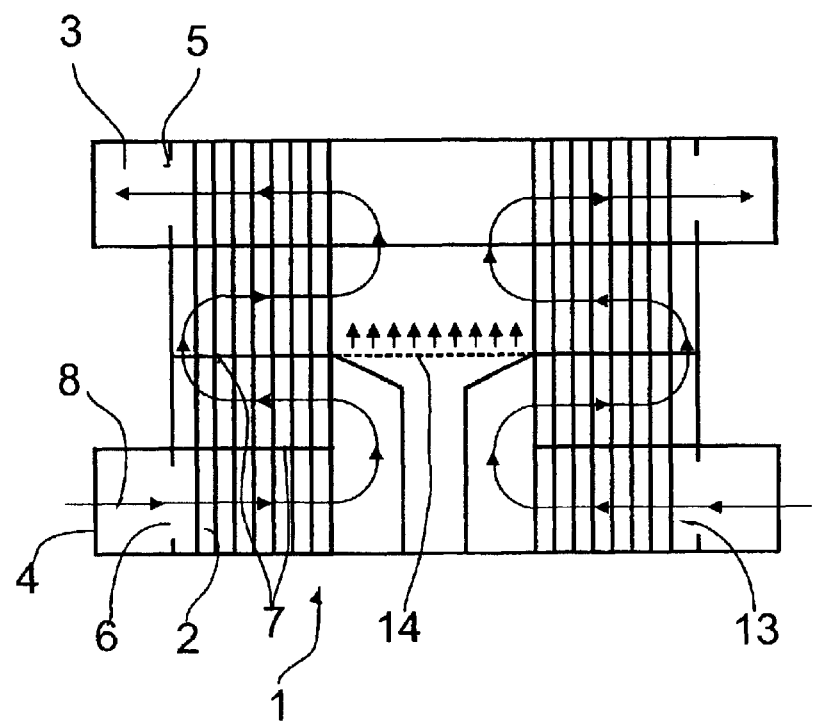
Figure 5:
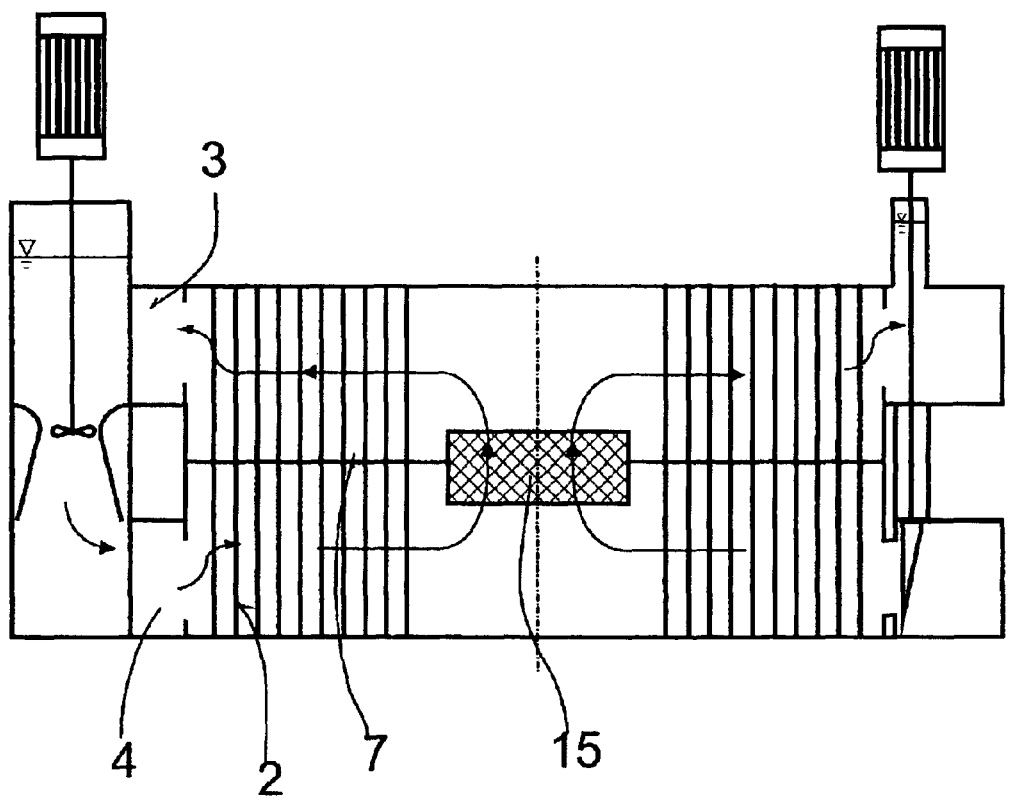

The invention is illustrated below with the aid of illustrative embodiments and a drawing. In the figures:

FIG. 1 shows a longitudinal section through a reactor having regulatable division of the heat transfer medium circuit via the lower ring line, FIG. 1a shows a cross section through the reactor of FIG. 1, FIG. 2 shows a longitudinal section through a reactor which has, by way of example, two further ring lines with regulatable introduction of heat transfer medium over the height of the reactor, FIG. 3 shows a longitudinal section through a reactor with introduction of a regulatable heat transfer medium stream via a radial chamber into the middle of the reactor, having the cross section in FIG. 3a, FIG. 4 shows an embodiment with two radial chambers arranged in the form of a cross, having the cross section in FIG. 4a, and FIG. 5 shows a further embodiment with static mixers in the middle of the reactor.

FIG. 1 shows a cylindrical reactor 1 having a vertical bundle of catalyst tubes 2 which leaves an inner space free in the middle of the cylinder, with a lower ring line 4 to which heat transfer medium is supplied and with an upper ring line 3 via which the heat transfer medium is removed, where the introduction and removal of the heat transfer medium occurs via openings 5 and 6 through the wall, and with deflecting plates 7 which make the heat transfer medium circuit follow a meandering path.

In these respects, the structure of the reactor is known from the prior art.

According to the present invention, a horizontal dividing wall 8 having openings 9 with a regulatable open cross section is provided in the region of the lower ring line 4. As can be seen from the cross section in FIG. 1a, the openings 9 are preferably distributed symmetrically over the reactor cross section. Furthermore, the preferred geometry of the openings 9 (circular) can be seen from FIG. 1a.

In the particular embodiment shown in longitudinal section in FIG. 2, two further ring lines 10 which are preferably equally spaced over the height of the reactor are provided, so as to allow material to pass between these further ring lines 10 and the lower ring line 4 via the feed lines 11 and the openings with a regulatable open cross section 9.

FIG. 3 shows a longitudinal section through an embodiment having a radial chamber 12 extending over the entire height of the reactor, preferably having a width b, with regulatable feed opening 13 for the heat transfer medium from the lower ring line 4 and a central outlet 14 for the heat transfer medium at a regulatable height in the middle of the reactor.

On the other hand, FIG. 4 shows a longitudinal section and FIG. 4a shows a cross section of a particular embodiment having two radial chambers 12 arranged in the form of a cross.

FIG. 5 schematically shows a longitudinal section of a reactor in which a static mixer is arranged in the middle of the reactor in the region where the deflecting plates 7 leave free an open cross section.

We claim:

1. A reactor which has a bundle of catalyst tubes and in which a heat transfer medium is circulated through the space surrounding the catalyst tubes, with ring lines at both ends of the reactor with openings through the wall for introduction or removal of a heat transfer medium by means of one or more pumps, where the heat transfer medium is introduced into the lower ring line and is returned via the upper ring line to the pump and the heat transfer medium or a substream of the heat transfer medium may, if desired, be passed over one or more external heat exchangers, and with deflecting plates which alternately leave free an open cross section in the middle of the reactor and at the edge of the reactor, wherein the lower ring line is divided by means of a horizontal dividing wall into two regions between which material can pass via preferably uniformly distributed openings having a regulatable open cross section.

2. A reactor as claimed in claim 1, wherein one or more further ring lines for the introduction in each case of regulatable substreams of the heat transfer medium stream from the lower ring line via regulatable openings in the horizontal dividing wall of the lower ring line and also suitable feed lines to the further ring lines are provided, distributed over the height of the reactor, in the region between the lower ring line and the upper ring line.

3. A reactor which has a bundle of catalyst tubes and in which a heat transfer medium is circulated through the space surrounding the catalyst tubes, with ring lines at both ends of the reactor with openings through the wall for introduction or removal of a heat transfer medium by means of one or more pumps, where the heat transfer medium is introduced into the lower ring line and is returned via the upper ring line to the pump(s) and the heat transfer medium or a substream of the heat transfer medium may, if desired, be passed over one or more external heat exchangers, and with deflecting plates which alternately leave free an open cross section in the middle of the reactor and at the edge of the reactor, wherein at least one radial chamber which extends over the entire height of the reactor and has a regulatable feed opening for the heat transfer medium from the lower ring line and a central outlet for the heat transfer medium at a settable height in the middle of the reactor is provided.

4. A reactor as claimed in claim 3, wherein the lower ring line is divided by means of a horizontal dividing wall into two regions between which material can pass via preferably uniformly distributed openings having a regulatable open cross section.

5. A reactor as claimed in claim 4, wherein one or more further ring lines for the introduction in each case of regulatable substreams of the heat transfer medium stream from the lower ring line via regulatable openings in the horizontal dividing wall of the lower ring line and also suitable feed lines to the further ring lines are provided, distributed over the height of the reactor, in the region between the lower ring line and the upper ring line.

6. A reactor as claimed in claim 3, which has two radial chambers arranged in the form of a cross.

7. A reactor as claimed in claim 3, wherein the width b of the chamber(s) is in the range from 100 mm to 500 mm.

8. A reactor as claimed in claim 1, wherein static mixers are located in one or all regions in the middle of the reactor where the deflecting plates leave free an open cross section.

9. A method for carrying out oxidation reactions by using a reactor as claimed in claim 1.

10. A reactor as claimed in claim 1, wherein the openings are uniformly distributed.

11. A reactor as claimed in claim 4, wherein the openings are uniformly distributed.

12. A reactor as claimed in claim 7, wherein the width of the chamber(s) is 100 mm.

13. A method as claimed in claim 9, for preparing phthalic anhydride, maleic anhydride, glyoxal, acrolein, methacrolein, acrylic acid and methacrylic acid.

* * * * *